United States Patent
Rodriguez Sanjuan

(10) Patent No.: US 9,486,129 B2
(45) Date of Patent: Nov. 8, 2016

(54) METHOD AND APPARATUS FOR CLEANING AN ENDOSCOPE

(71) Applicant: Risen Star Industries, LLC, McAllen, TX (US)

(72) Inventor: Jose Rodriguez Sanjuan, McAllen, TX (US)

(73) Assignee: Risen Star Industries, LLC, McAllen, TX (US)

( * ) Notice: Subject to any disclaimer, the term of this patent is extended or adjusted under 35 U.S.C. 154(b) by 480 days.

(21) Appl. No.: 13/781,091

(22) Filed: Feb. 28, 2013

(65) Prior Publication Data

US 2013/0305469 A1   Nov. 21, 2013

Related U.S. Application Data

(60) Provisional application No. 61/604,815, filed on Feb. 29, 2012.

(51) Int. Cl.
*B08B 9/04* (2006.01)
*A61B 1/12* (2006.01)

(52) U.S. Cl.
CPC .............. *A61B 1/122* (2013.01); *A61B 1/126* (2013.01); *B08B 9/04* (2013.01); *A61B 2090/701* (2016.02)

(58) Field of Classification Search
CPC ........ B08B 9/04; B08B 9/0436; A61M 5/00; A61B 2090/701
See application file for complete search history.

(56) References Cited

U.S. PATENT DOCUMENTS

| | | | |
|---|---|---|---|
| 4,889,106 A * | 12/1989 | Watanabe | A61B 10/04 15/104.2 |
| 5,168,593 A * | 12/1992 | Poje | A46B 3/18 15/104.2 |
| 5,311,639 A | 5/1994 | Boshier | |
| 5,392,766 A | 2/1995 | Masterson et al. | |
| 5,407,423 A * | 4/1995 | Yoon | 604/1 |
| 5,615,439 A * | 4/1997 | Bourrelly | A46B 3/18 15/104.2 |
| 6,755,782 B2 | 6/2004 | Ogawa | |
| 7,979,943 B2 * | 7/2011 | Arai | A61B 1/122 15/104.05 |
| 8,001,984 B2 | 8/2011 | Sasaki | |
| 8,262,645 B2 * | 9/2012 | Bagwell et al. | 604/540 |
| 8,479,344 B2 * | 7/2013 | Maslanka | A61B 1/122 15/104.05 |
| 8,490,235 B2 * | 7/2013 | Soetermans | 15/104.05 |
| 2009/0250081 A1 * | 10/2009 | Gordin et al. | 134/6 |
| 2009/0264703 A1 * | 10/2009 | Pribanic | 600/121 |
| 2013/0031735 A1 * | 2/2013 | Brand et al. | 15/104.93 |

\* cited by examiner

*Primary Examiner* — Randall Chin

(57) ABSTRACT

An apparatus for cleaning an endoscope that may include a handle, a rod insertable into a channel of an endoscope, the rod including a first end and a second end, the first end of the rod being attachable to the handle, a wiping tip insertable into the endoscope channel and attachable to the second end of the rod, and a wiping surface attachable to the wiping tip.

8 Claims, 17 Drawing Sheets

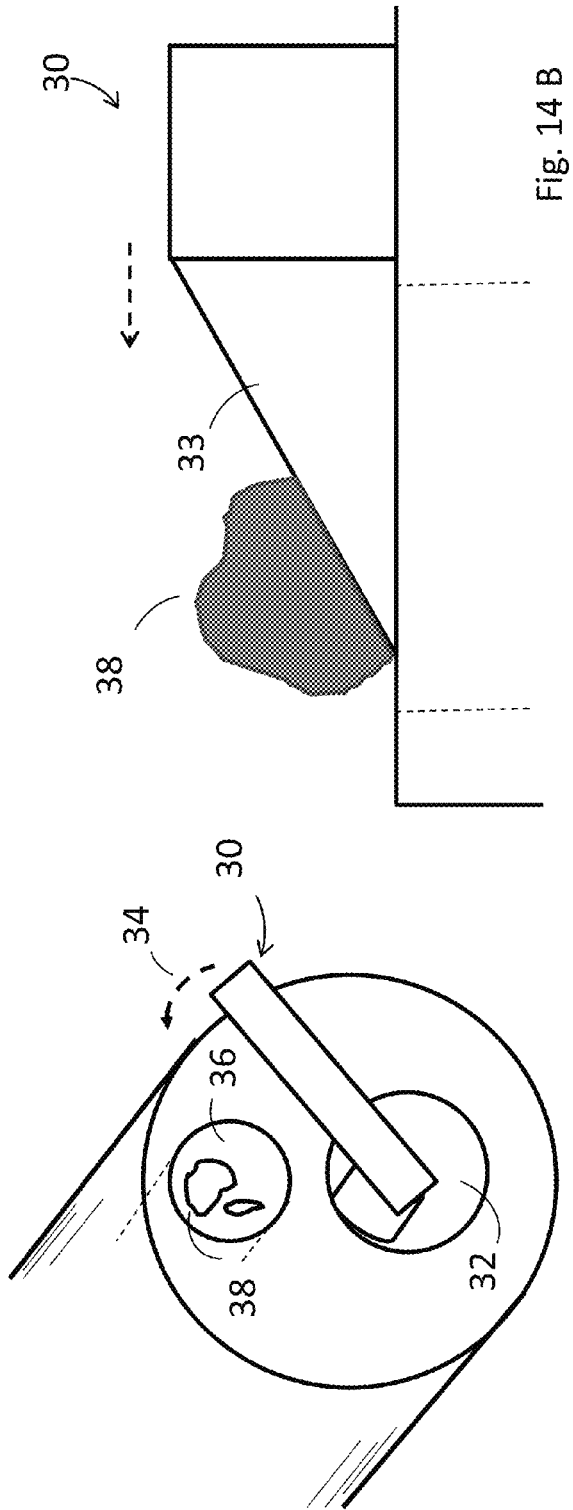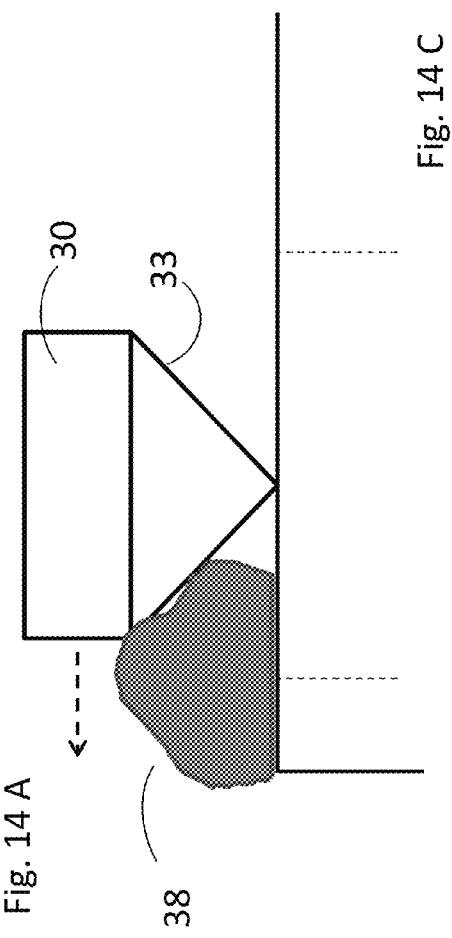
Fig. 14 A
Fig. 14 B
Fig. 14 C

METHOD AND APPARATUS FOR CLEANING AN ENDOSCOPE

CROSS REFERENCE TO RELATED APPLICATIONS

This application claims priority to U.S. Provisional Application Ser. No. 61/604,815 filed Feb. 29, 2012. The disclosure of the aforementioned application is incorporated herein by reference.

BACKGROUND

During insertion and/or movement of an endoscope within a body cavity, material, e.g., humors, blood, mucous or debris, may become lodged on or near an optical element or other distal portion of an endoscope. In such a situation, an operator's field of view may become partially or wholly obstructed. To remove such obstruction, water or another fluid may be flushed through an endoscope channel in an attempt to clean optical elements. However, such washings may be only partially successful and may not be desirable for some types of procedures. In other cases, an operator may attempt to remove obstructing debris using mechanical agitation, e.g., by gently contacting the distal end of the endoscope with a nearby, internal body surface. However, such action carries a risk of inadvertent damage to the contacted tissue. There remains a need for a convenient and effective method and apparatus for removing debris from optical or other functional elements of an endoscope.

BRIEF DESCRIPTION OF THE DRAWINGS

FIGS. 14A-14C illustrate various embodiments of apparatuses that includes blade-shaped wiping surfaces.

DETAILED DESCRIPTION

The method and apparatus described herein may be used to clean the distal end of an endoscope. The apparatus may, for example, be inserted through either a channel of an endoscope, and may be used to mechanically clean or facilitate cleaning of the endoscope. In some embodiments, the method and apparatus of cleaning described herein may be used individually or in combination with other instruments or methods for cleaning an endoscope. For example, the apparatus may, in some embodiments, be used in connection with suction and/or a washing fluid to assist in cleaning.

Figure 1:
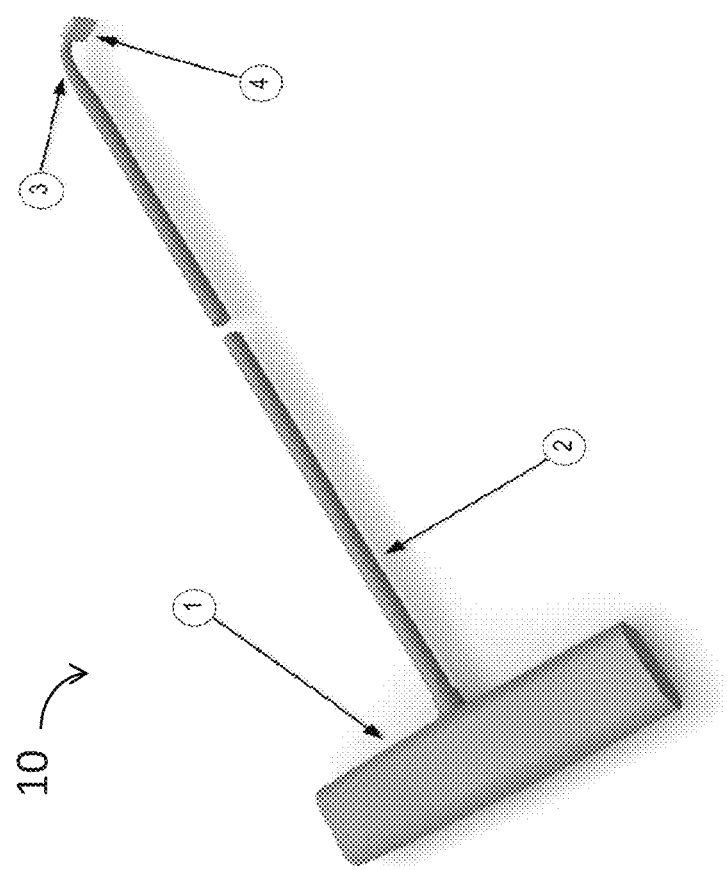
FIG. 1 illustrates one embodiment of an apparatus for cleaning an endoscope.

FIG. 1 illustrates an exemplary embodiment of an endoscope cleaning apparatus (10). The apparatus may comprise one or more portions which may be inserted through an endoscope channel. For example, an apparatus may comprise a rod configured at one end to hold a squeegee or wiping surface. In some embodiments, the angled end (such as shown in the embodiment of FIG. 14B) and/or the squeegee or wiping surface may be reversibly foldable so that it may be inserted and retracted during operation. As shown in FIG. 1, an apparatus (10) may include a handle (1), a rod (2), a wiping tip (3), and a wiping surface (4). In some embodiments, the handle (1), rod (2) and wiping tip (3) may be a unitary piece of flexible bio safe plastic. In some embodiments, the wiping tip (3) may be interchangeable with other tips attachable to the rod. For example, the wiping tip (3) may be removably affixed to the rod, such as by threaded attachment, so as to allow for disposal of wiping tips after use. The handle may also, in some embodiments, be removable from the rod (2). Similarly, the wiping surface may be of unitary construction with the wiping tip, or permanently or removably attached to the wiping tip.

Figure 2:
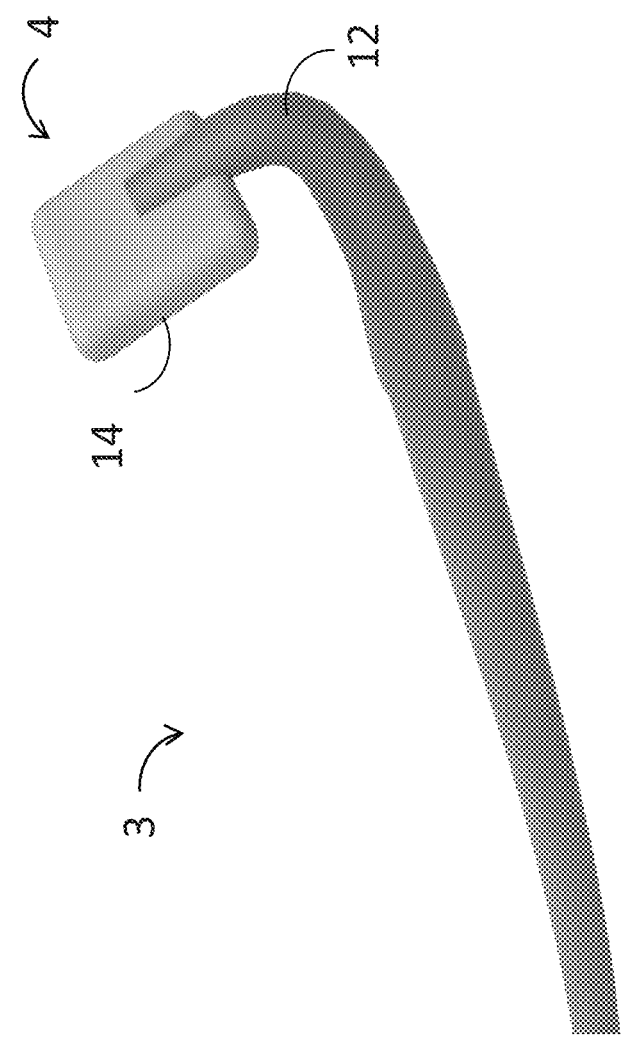
FIG. 2 illustrates the wiping tip portion of the embodiment of FIG. 1.

An expanded view of an embodiment of the wiping tip (3) and wiping surface (4) is shown in FIG. 2. The wiping surface (4) may take a variety of forms. For example, and without limitation, the wiping surface may comprise a smooth cloth, cloth with large loop fibers (such as a towel), porous cloth (such as gauze), sponge-like material, brush with bristles, rake, rigid edge, flexible polymer piece (such as a squeegee), gun cloth, another surface appropriate for removing debris or combinations thereof.

The wiping surface (4) may be affixed to the wiping tip (3) in any of various ways. For example, the wiping tip may include a clamp or aperture for permanently or removably holding the wiping surface. In other embodiments, the wiping surface may be affixed to the wiping tip with a biosafe adhesive or glue, or may be affixed in some other suitable manner. In some embodiments, an integral bond between the wiping tip (3) and the wiping surface (4) may be present. For example, the wiping surface may be a flexible polymer that is connected to the wiping tip, and may be sterilized between applications for reuse. The wiping tip may include a portion, e.g., the region of bend (12), that is under tension and may, upon exiting from an endoscope channel (not shown), relax and direct a wiping region (14) of wiping surface (4) to achieve an orientation that may be substantially parallel (or at some other suitable angle) to an outer face of the endoscope (not shown), e.g., a surface that may need cleaning.

Figure 3:
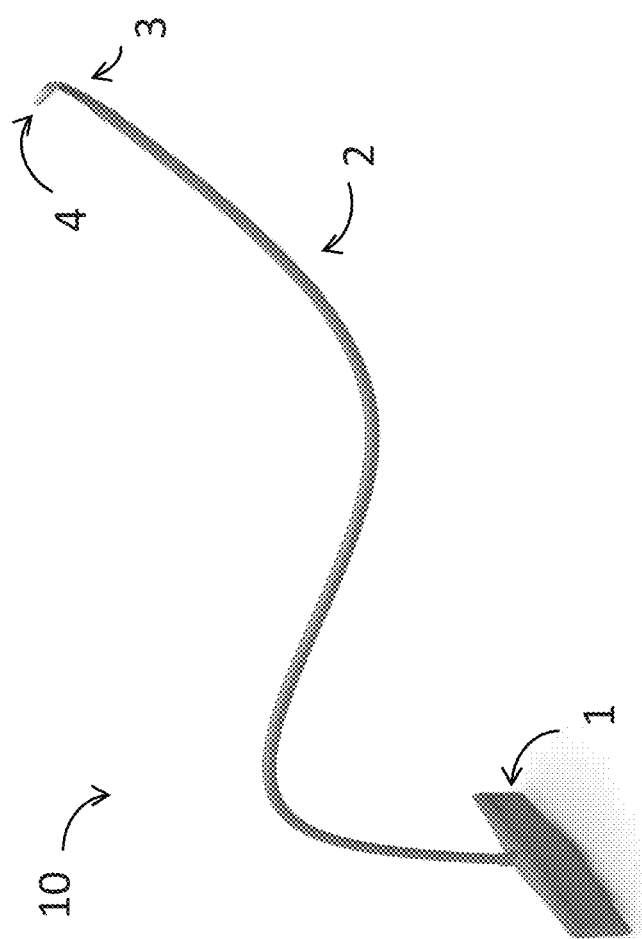
FIG. 3 illustrates the embodiment of FIG. 1 in an elastically deformed configuration.

The apparatus may be elastically or inelastically deformable to facilitate insertion of the wiping tip and at least a portion of the rod into an endoscope channel. For example, FIG. 3 illustrates an embodiment of an apparatus for cleaning an endoscope surface, the apparatus being in a deformed configuration. Such deformation may assist an operator in navigating the turns and curves which may be associated with use of an endoscope. In some embodiments, the rod may be capable of being elastically deformed; however, the rod may also be stiff enough to transfer rotational and/or axial forces between the handle (1) and the wiping tip (3). The handle (1) may, in some embodiments, apply either or both of a rotational and/or an axial force to the rod (2) for any of insertion, extraction or actuation of the wiping tip (3).

Figure 4:
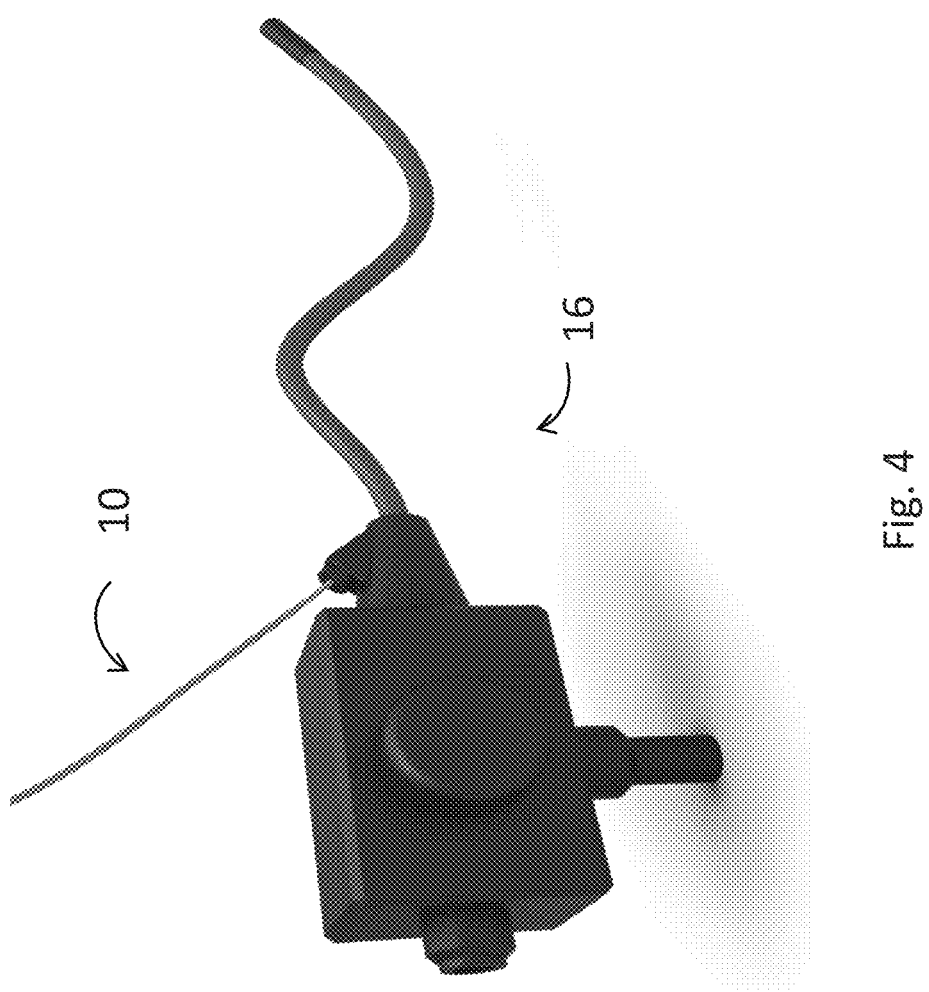
FIG. 4 illustrates insertion of the embodiment of FIG. 1 into an endoscope channel.

As illustrated in FIG. 4, such an apparatus (10) may be insertable into an endoscope (16). The apparatus (10) may be inserted and extracted any number of times during a procedure, e.g., as needed to clean the distal end of the endoscope. In some embodiments, the endoscope cleaning apparatus may be inserted through an endoscope, used to clean the outer distal end of the endoscope, and then fully retracted and removed from the endoscope channel. Retraction of the apparatus and removal of the apparatus from a given endoscope channel may free up that particular channel for use in another purpose or application. Such features may make some embodiments described herein particularly valuable for procedures that demand an extremely narrow endoscope.

In other embodiments, retraction of the apparatus may involve only partial retraction of the wiping tip. For example, the wiping tip may be retracted into an endoscope channel, e.g., to prevent the wiping surface from blocking the endoscope image or to prevent the distal portion of the apparatus from interference with a medical procedure, but not fully removed from the endoscope channel. Alternatively, in some embodiments, the wiping tip may be extended beyond the distal portion of the endoscope channel and/or rotated to move the wiping tip (and wiping surface) beyond the active field of view or region of interest to an operator. In some embodiments, the apparatus or a portion of the apparatus may be inserted into an endoscope channel prior to introduction of the endoscope into a body cavity. Thus, as the endoscope is manipulated during insertion or routing through an internal cavity the cleaning apparatus would be manipulated in a corresponding manner.

Figure 5:
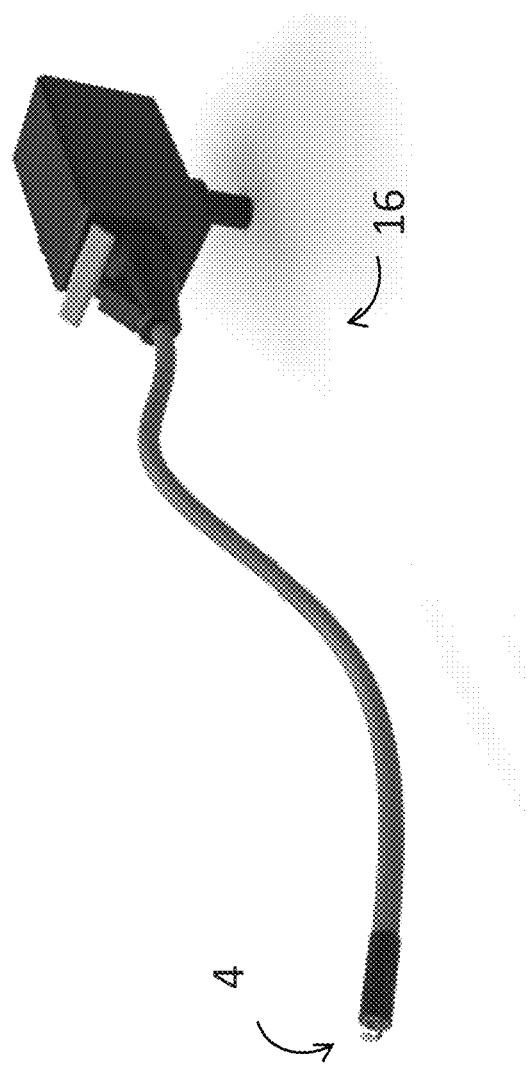
FIG. 5 illustrates the embodiment of FIG. 1 inserted into an endoscope channel and exiting the distal portion of the endoscope.

As illustrated in FIG. 5 the cleaning apparatus may be fully inserted through an endoscope such that the wiping tip of the apparatus exits the distal end of the endoscope. On exit of the wiping tip of the apparatus from a channel of the endoscope the apparatus may, in some embodiments, return to operating form, e.g., the wiping tip may orient to an angle which enables it to reach the endoscope lens. The tip may, in some embodiments, orient to be approximately perpendicular to the axis of the rod, or at some other suitable angle thereto, and may facilitate a wiping action once torque or motion is applied at an external handle. In operation, the external handle may protrude from the endoscope and extend beyond the channel in which the cleaning apparatus is inserted. The extension of the handle may, e.g., permit the handle to clear the scope, without obstruction, upon rotation of the handle. The external handle may, e.g., extend from the endoscope by about 12 cm or by some other convenient length.

Figure 6:
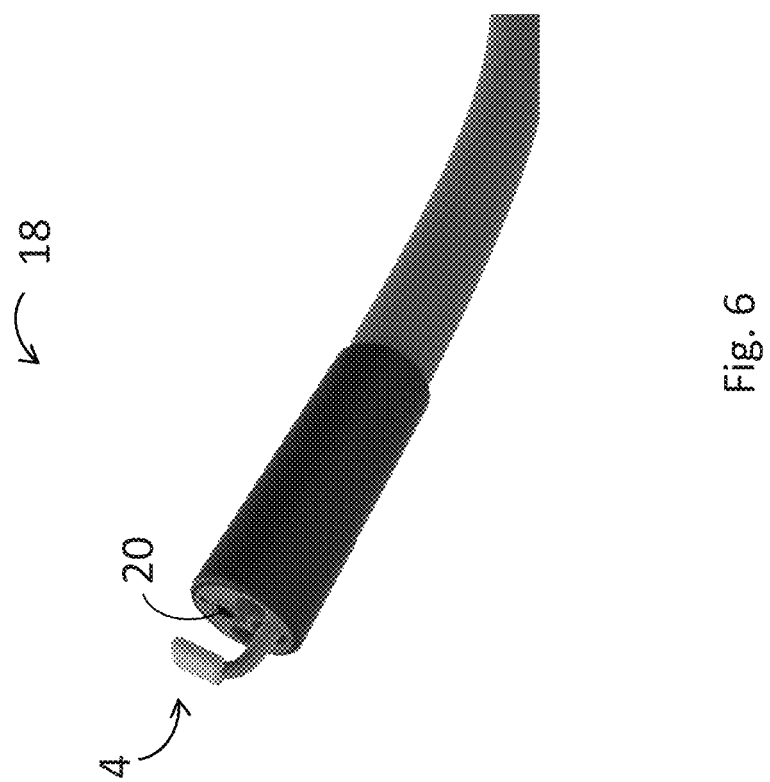
FIG. 6 illustrates a more detailed view of the embodiment of FIG. 1 exiting the distal portion of an endoscope.

FIG. 6 illustrates a more detailed view of one embodiment of the exiting portion of the cleaning apparatus and in a hyper-extended configuration (18). As shown in FIG. 6, the wiping surface (4) may be extended away from a channel with an optical surface (20). In some embodiments, the relative sizes of the wiping surface (4) and wipe tip (3) may be sufficient such that rotation of the wiping surface, e.g., by manipulation of the handle, allows the operator to view a region of interest. In some embodiments, the wiping tip may be deformed to fit within an endoscope channel. For example, the wiping tip may be folded against the rod, or deformed to lie generally along an axis of the rod so as to allow insertion of the wiping tip and rod into an endoscope channel. Upon exiting the channel at the distal end of the endoscope, the wiping tip may return to its non-deformed configuration, e.g., as shown in FIG. 6.

Figure 7:
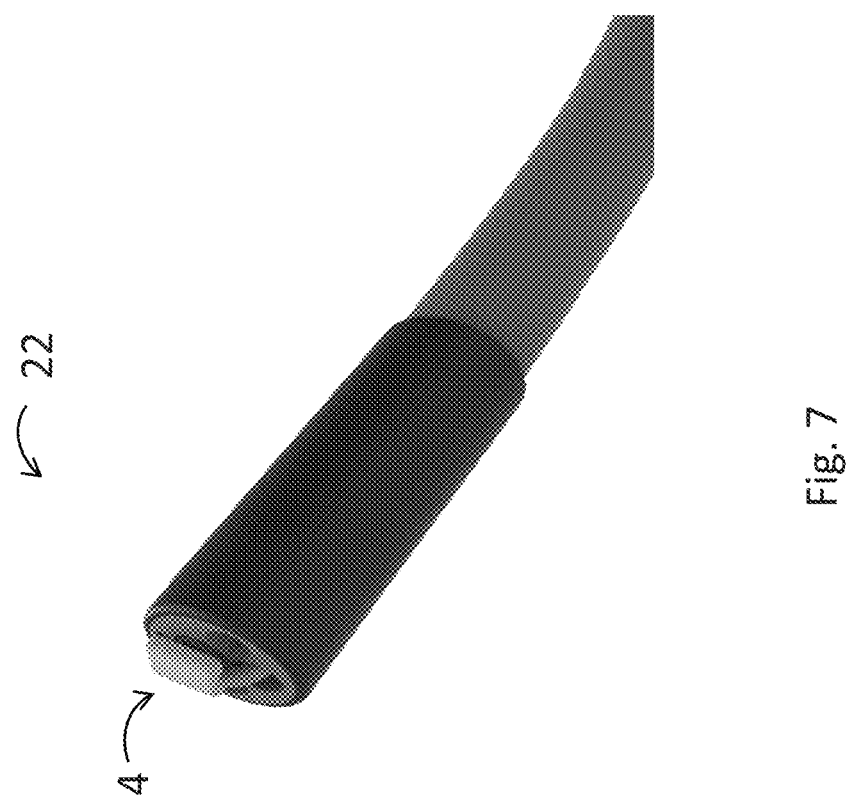
FIG. 7 illustrates the wiping tip portion of the embodiment of FIG. 1 oriented against an optical surface of an endoscope.

FIG. 7 illustrates the embodiment of FIG. 6, in which the wipe tip and wipe surface are in a wipe position (22) against the distal end of the endoscope. As shown in FIG. 7 the wiping surface (4) may be manipulated, through rotational and axial movement of the rod, to contact a particular region of the distal end of an endoscope, such as an optical surface. Thus in contact, the wiping surface may be moved across the distal end of the endoscope so as to effect cleaning thereof. In some embodiments, pressure may be applied to the end of the endoscope by the wiping tip by gently pulling on and rotating the rod handle, thereby allowing for a more aggressive wiping or scrubbing action.

Figure 8:
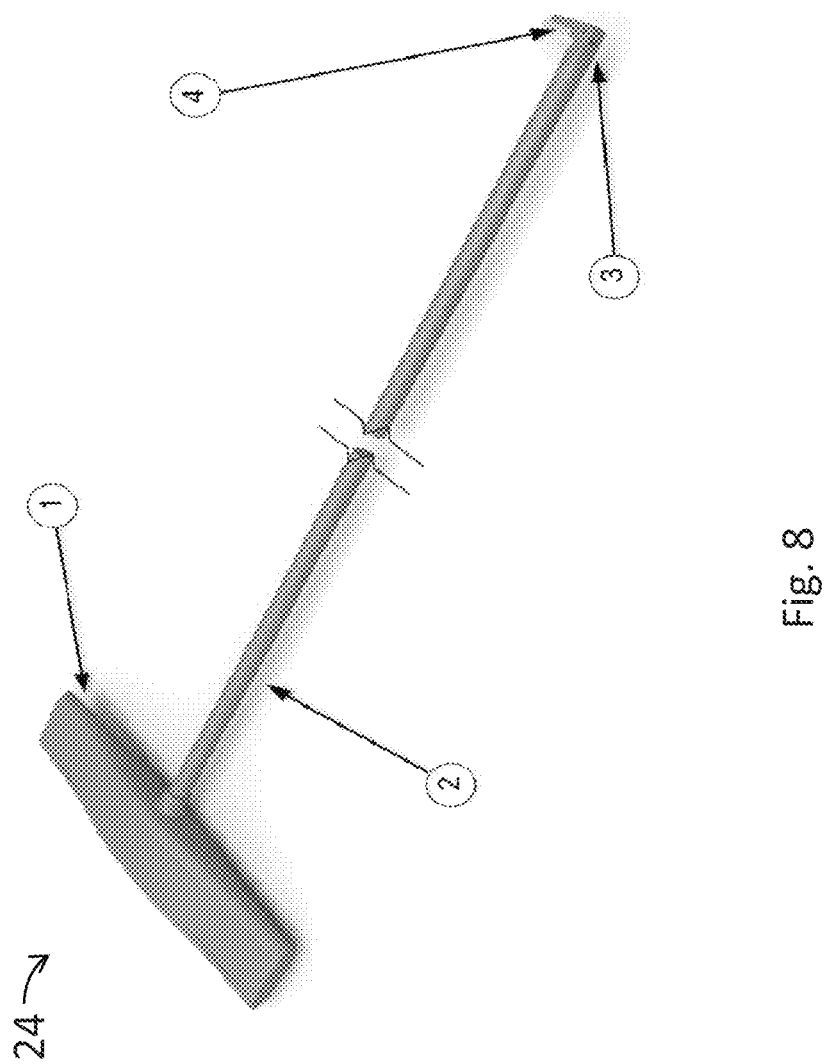
FIG. 8 illustrates another embodiment of an apparatus for cleaning an endoscope in which the wiping tip includes a hinge.
Figure 9:
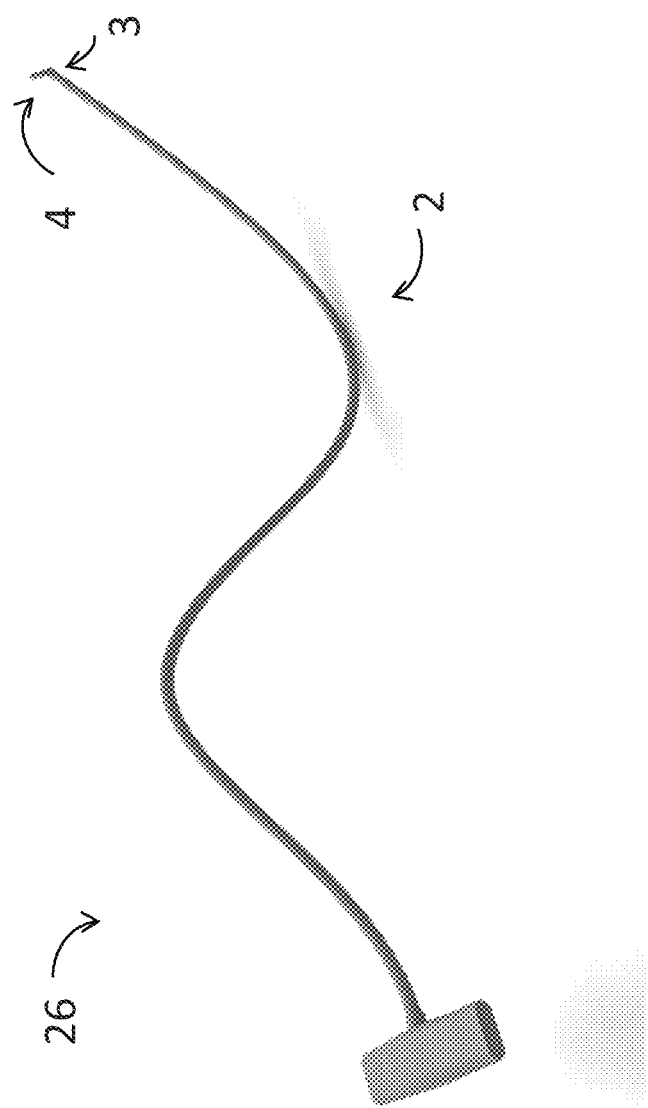
FIG. 9 illustrates a view of the embodiment of FIG. 8 in an elastically deformed configuration.

FIG. 8 illustrates another exemplary embodiment of an endoscope cleaning apparatus (24). The cleaning apparatus of FIG. 8 comprises a handle (1), rod (2), wiping tip (3), and wiping surface or squeegee (4). The wiping tip may, in some embodiments, include a hinge to allow the wiping tip to more readily deform for insertion into an endoscope channel, and return to an undeformed configuration upon exiting the channel. FIG. 9 illustrates a more detailed view of the endoscope cleaning apparatus of FIG. 8 having the rod portion thereof in a deformed configuration (26).

Figure 10:
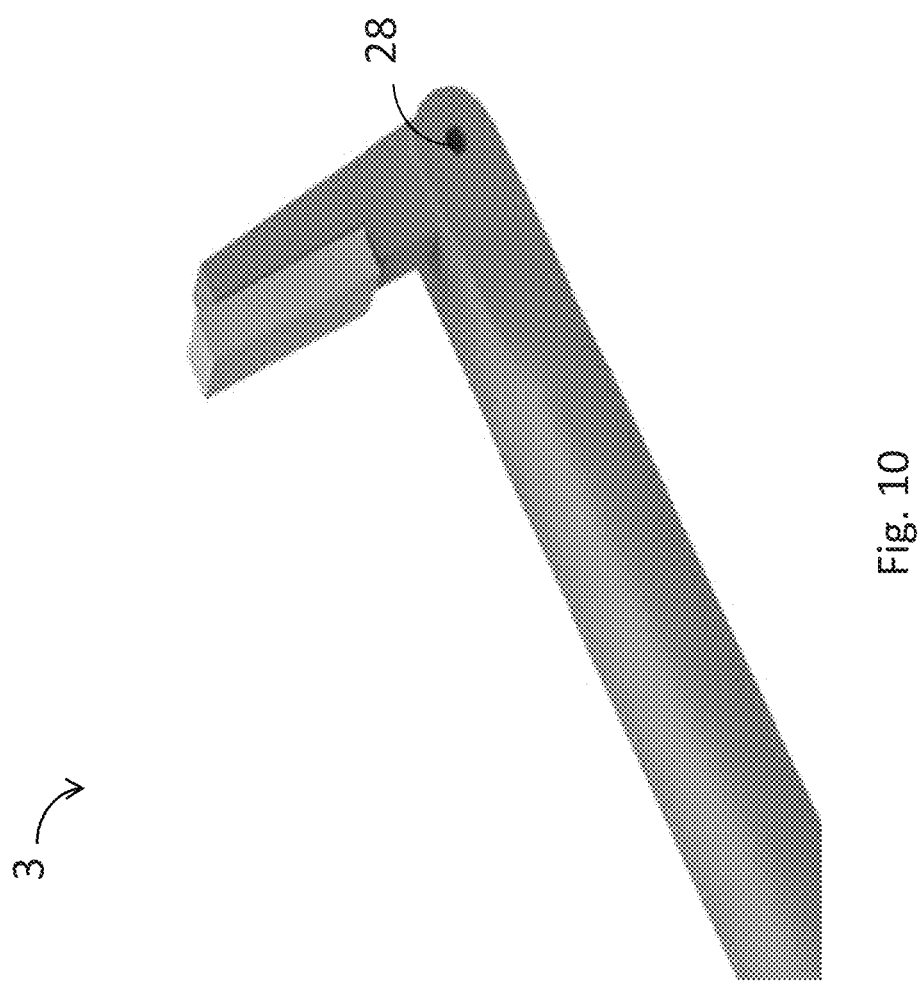
FIG. 10 illustrates the wiping tip portion of the embodiment of FIG. 8.
Figure 11:
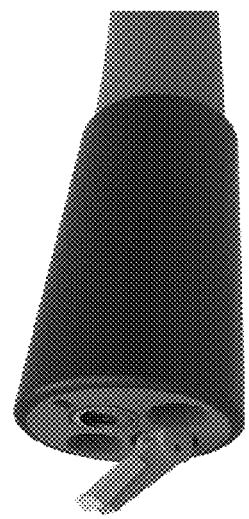
FIGS. 11A-11C illustrate the embodiment of FIG. 10 as it deploys at the distal end of an endoscope.
Figure 11:
Figure 11:

FIG. 10 illustrates a more detailed view of the wiping tip (3) of the apparatus (24). As shown in FIG. 10, the wiping tip may include a hinge (28). The hinge may include a spring or other elastically deformable urging mechanism to allow the wiping tip to deform and spring back to shape, as shown in FIGS. 11A-C (two-part hinge embodiment), to facilitate insertion of the apparatus into a channel of an endoscope. In some embodiments, the springing hinge linkage may return to a deployed position upon exit of the forward end of the endoscope channel. In this position the tip may be capable of being actuated, e.g., rotated axially, to wipe the lens or another element of the endoscope. For example, as shown in FIG. 11A, the hinged wiping tip of the apparatus may be inserted through an endoscope channel in a flattened configuration. Upon exiting the endoscope channel the hinged tip may return to a deployed position (FIGS. 11B and 11C). In some embodiments, the hinge may comprise two or more parts connected by a pin, or comprise a single part capable of elastic deformation (such as the wiping tip 3 of FIG. 2 having a bend 12 that may be flattened for insertion of the wiping tip into an endoscope) for insertion through an endoscope channel. Whether of one or more parts, the hinge may comprise a spring or spring-like material property to urge the wiping tip into a deployed position upon exiting the endoscope channel. A deployed position may be preset or predetermined. In other embodiments, the hinge may not comprise spring-like forces so as to allow on operator to deploy the wiping tip at a desired position. In such embodiments, the hinge may comprise frictional interfaces that allow deployment of the wiping tip manually by the operator and maintain the wiping tip in a substantially deployed position. When deployed, the wiping tip may be substantially perpendicular to the rod, or at any angle to the rod suitable for urging the wiping tip against an optical lens or other element of the endoscope. For example, a suitable angle may be an acute angle so that when the cleaning apparatus external handle is pulled away from the endoscope channel, the wiping may be urged against the end of the endoscope with sufficient pressure to deform the wiping tip to better conform to the contour of the endoscope end.

Figure 12:
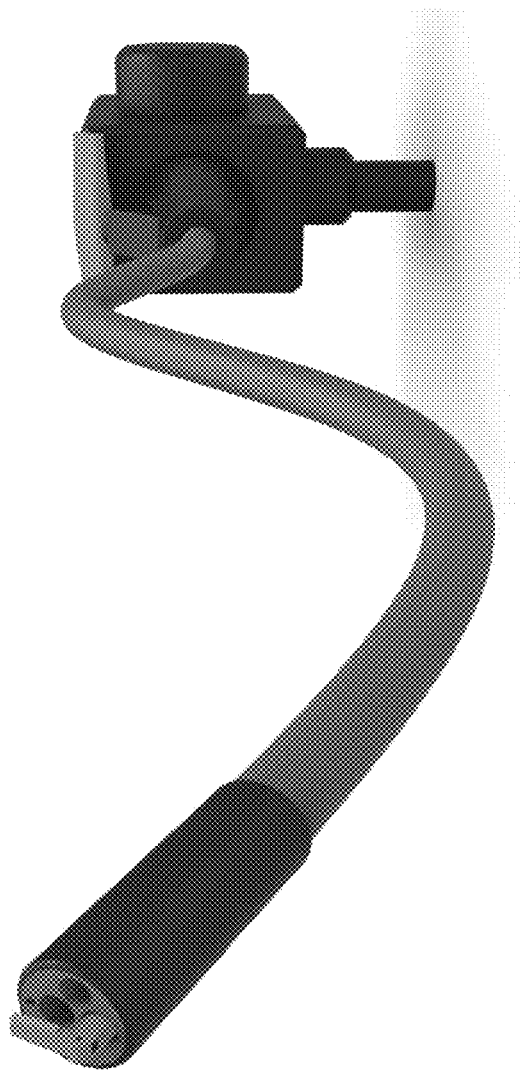
FIG. 12 illustrates an endoscope and the embodiment of FIG. 8 inserted through a channel in the endoscope.
Figure 13:
FIG. 13 illustrates a more detailed view of the distal portion of the embodiment of FIG. 12 exiting an endoscope and oriented in a position for wiping an optical lens.

FIG. 12 shows the wiping tip of one embodiment of the cleaning apparatus extending through an endoscope channel and oriented in a wiping position. FIG. 13 shows a more detailed view of the hinged wipe tip of the apparatus oriented in a deployed position to clean a portion of the endoscope tip. Actuation may, in some embodiments, be facilitated by applying torque/rotating motion on the actuating handle, e.g., at the opposite end of the apparatus. In some embodiments, an operator may have control of the angle of the wiping tip, such as by use of a control cable (not shown) that runs through the rod and is attached at one end to the articulatable portion of the wiping tip. For example, as the cable is pushed or pulled, the angle of the wiping tip may be adjusted accordingly. In some embodiments control of a cable may be accomplished manually. In some embodiments, the angle of the wiping tip may be controlled automatically, e.g., controlled electronically. For example, a motor may be controlled, such as, for example, by wireless methods. Such methods may provide the operator with direct control over the angle of the wiping tip. Similarly, insertion and deployment of the endoscope cleaning apparatus may be accomplished by automatic means, such as by servo motor. In operation, the external handle may protrude from the endoscope and extend beyond the channel in which the cleaning apparatus is inserted. The extension of the handle may, e.g., permit the handle to clear the scope, without obstruction, upon rotation of the handle. The external handle may, e.g., extend from the endoscope by about 12 cm or by some other convenient length.

The endoscope cleaning apparatus may be used in a variety of ways. For example, the apparatus may be inserted into a channel of an endoscope as described above, and deployed against the distal end of the endoscope. The wiping surface may be moved, via manipulation of the handle and rod, against the end of the endoscope to clean, e.g., an optical lens. In some embodiments, an endoscope may include multiple channels. The endoscope cleaning apparatus may be deployed through one channel, and a fluid, such as water or air, may be provided through another channel. The wiping tip of the apparatus may be directed into the path of fluid flowing from the fluid channel so as to re-direct fluid onto another part of the distal end of the endoscope, such as an optical lens. Fluid splashing off of or redirected from the wiping tip may serve to soften or dissolve debris stuck to the optical lens. The wiping tip may be used thereafter to further clean the optical lens through mechanical action. In some embodiments, the wiping surface may be configured to better redirect fluid from one endoscope channel to a surface on the distal end of the endoscope. A wiping surface may be, for example, partially curved or angled to redirect fluid.

The rod connecting the handle to the wiping tip may be of varying thickness, material and rigidity. For example, each end of the rod may be more rigid than the middle portions of the rod so as to allow better control of the wiping tip by the handle, and to allow for easier insertion and removal of the apparatus from the endoscope. Similarly, the rod may be of any cross-sectional configuration, such as round, polygonal, oval or hollow to allow for axial and rotational control of the wiping tip by the handle. In some embodiments, the rod may be tapered at one or both ends, or in the middle. In other embodiments, the rod may be hollow or contain a channel for communication of fluids therethrough. For example, a washing fluid may be directed through the cleaning apparatus and exit from the wiping tip to further effect cleaning of the distal end of the endoscope. The wiping tip may comprise a water jet configured to direct fluid against the distal end of the endoscope, in which embodiment a wiping surface may not be necessary. In such embodiments, a wiping tip may be optional. The rod may comprise any suitable material, such as plastic, rubber, silicone, polycarbonate, wire, metal, rope, cloth or paper, or any suitable material.

Figure 15:
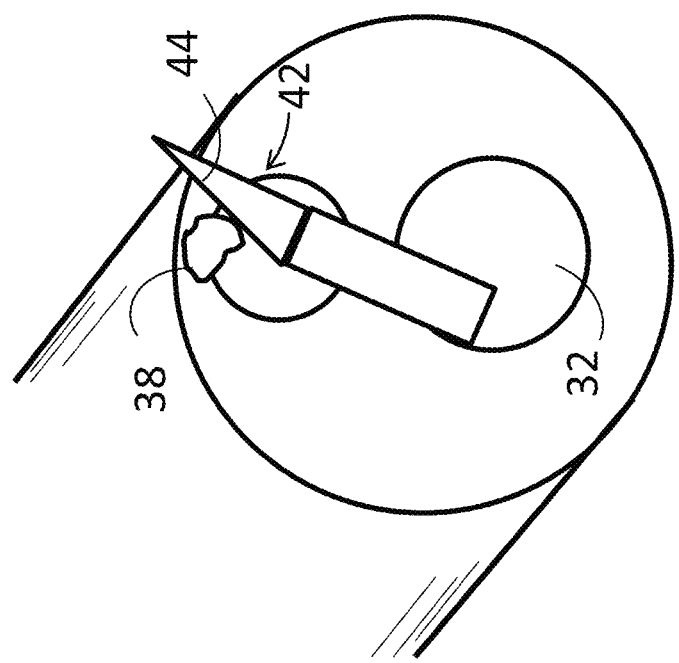
FIG. 15A-B illustrate various embodiments of apparatuses that include a blade-shaped wiping surface.
Figure 15:
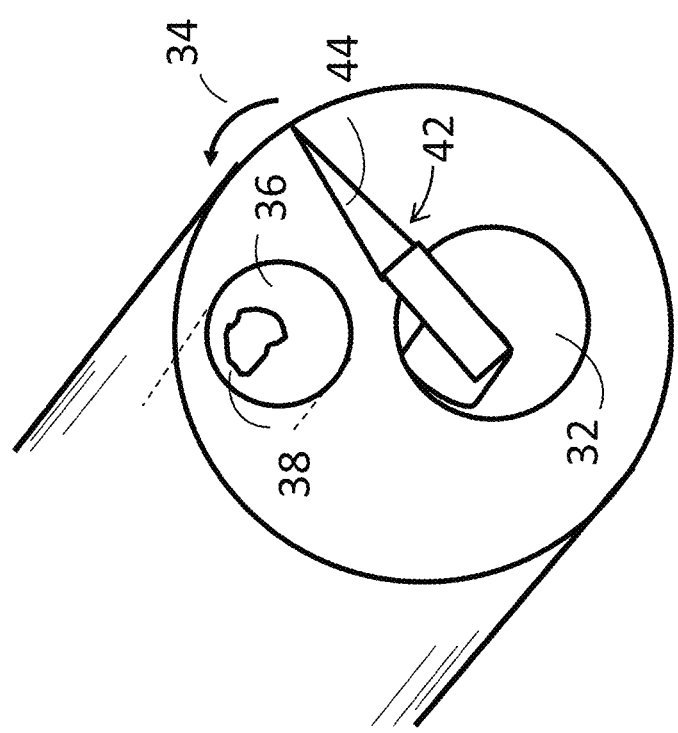

In some embodiments, a wiping tip may comprise a wiping surface contoured to match the outer end of an endoscope. In other embodiments, the wiping tip may comprise a wiping surface capable of conforming to a contour of the end of an endoscope. The wiping tip may, in some embodiments, comprise a surface that is configured such that rotation of the wiping tip moves debris, e.g., in a radial direction or in a direction that lifts debris from the endoscope surface, from the end of the endoscope, or both. For example, the wiping tip may, in some embodiments, comprise a surface that is blade-shaped. An embodiment of a cleaning apparatus with a blade-shaped wiping surface is, for example, shown in FIGS. 14A and 14B. In FIG. 14A a wiping tip 30 may extend from the channel 32. In some embodiments, the wiping tip 30 with blade-shaped wiping surface 33 may be moved in a direction 34 so as to contact and clear the outer face 36 of the endoscope optical lens. Movement of the wiping tip may, for example, initiate removal of debris element 38, such as by lifting (as shown in FIG. 14B) or scraping (as shown in FIG. 14C). FIGS. 15A and 15B illustrate yet another embodiment of a wiping tip 42 having a blade-shaped wiping surface 44. The wiping surface 44 may direct debris radially, e.g., towards the edge of the endoscope end.

Figure 16:
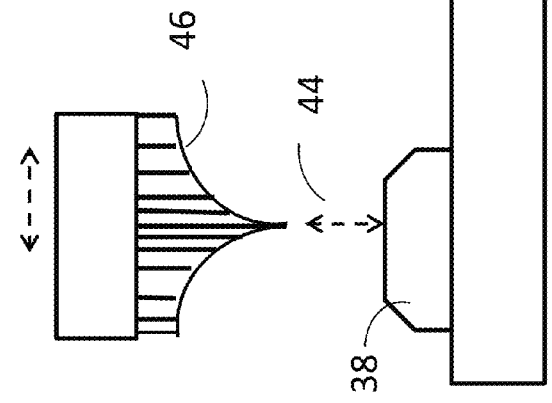
FIG. 16A-16C illustrate another embodiment of a method and apparatus for cleaning an endoscope.
Figure 16:
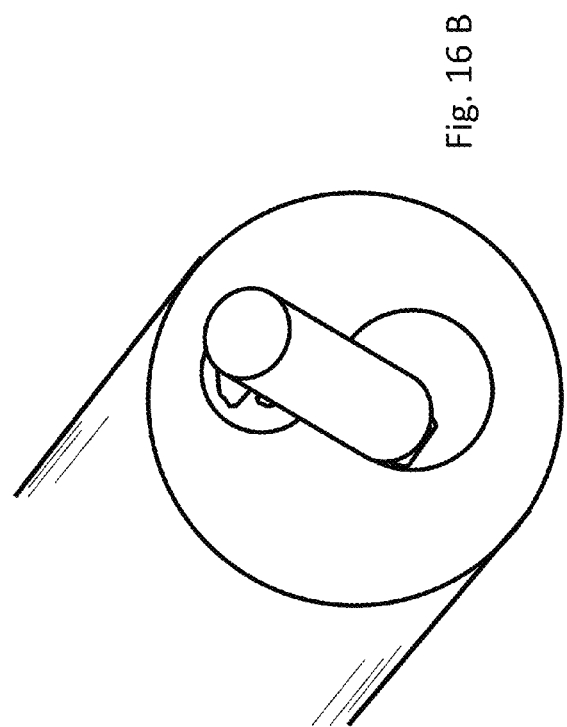
Figure 16:
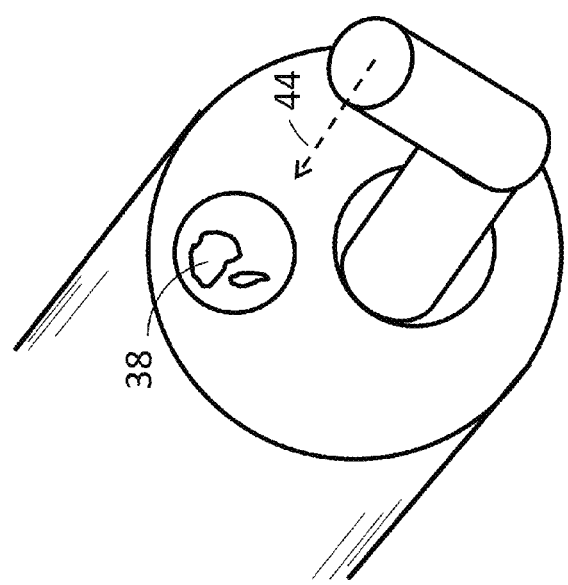

In some embodiments, a wiping apparatus may be inserted through an endoscope channel and pulled back in order to urge the wiping surface against the surface to be cleaned. For example, such operation may be understood in reference to FIGS. 16A-C. The wiping tip in FIG. 16A is shown to be inserted through an endoscope channel and as illustrated in FIG. 16B may be pulled back (along line 44) to urge the wiping surface toward the end of the endoscope and thus potentially in contact with debris. In the embodiment of FIGS. 16A and 16B the wiping tip may comprise a wiping surface having a variety of shapes, e.g., be curved, blade-shaped, squared or some other suitable configuration. In the embodiment of FIG. 16C, the wiping surface may be configured such that contact of the wiping surface with a particle of debris may serve to impale, break up or cut through debris particles. For example, the wiping surface 46 of FIG. 16C may comprise bristles of varying lengths, e.g., a blade shaped arrangement of bristles, or a flexible polymer, or a more rigid nylon material.

Figure 17:
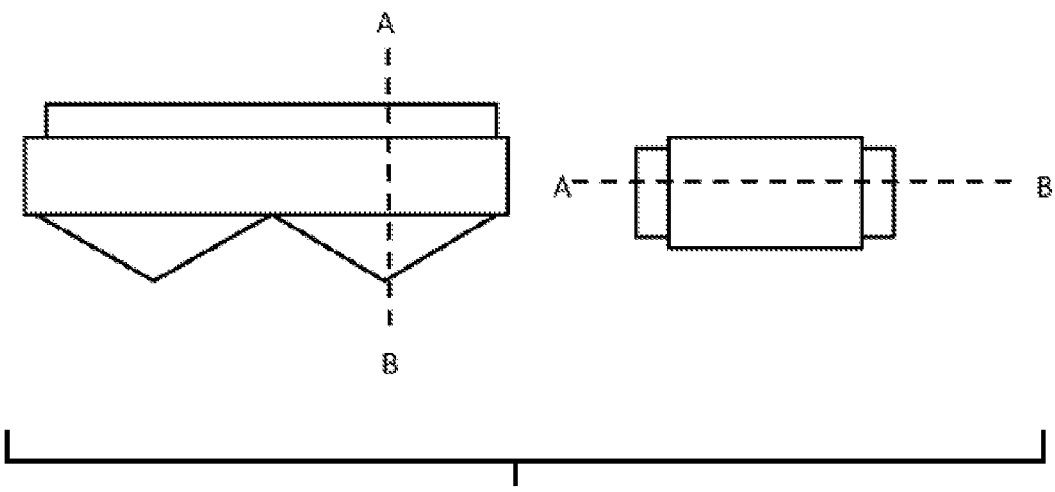
FIG. 17A-B illustrates further embodiments of wiping tips.
Figure 17:
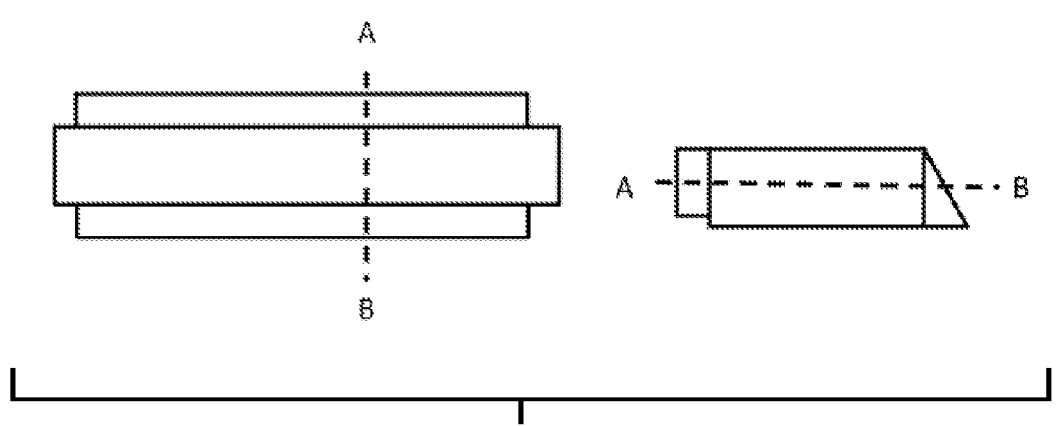

Various other embodiments of wiping tips are shown in FIG. 17. For example, (as illustrated in FIGS. 17A and 17B) a wiping tip may be configured in an asymmetric manner. An operator may, for example, choose to rotate a wiping apparatus in either a clockwise or counterclockwise direction in attempting to clear debris. The operator may, therefore, select to contact debris particles with one of two different surfaces depending upon the operator's personal preference or the nature of the debris that has become attached. A wiping surface may comprise any of various materials, e.g., flexible polymer piece, sponge-like material, bristles, cloth or other appropriate material as described above, and the surface shape may, e.g., be demarcated by the edge of the material or by the density and shape of bristles or cloth or other material used for the wiping surface.

Although the foregoing specific details describe certain embodiments, persons of ordinary skill in the art will recognize that various changes may be made in the details of these embodiments without departing from the spirit and scope of this invention and considering the doctrine of equivalents. Therefore, it should be understood that this invention is not limited to the specific details shown and described herein.

What is claimed is:

1. An apparatus for cleaning an endoscope comprising:
   a handle;
   a rod insertable into a channel of an endoscope having a distal end, the rod comprising a first end and a second end, the first end of the rod being attachable to the handle;
   a wiping tip insertable into the endo scope channel and attached to the second end of the rod, the wiping tip having a preset orientation substantially conforming to a surface of the distal end of the endoscope when the wiping tip is extended from the channel and further comprising a hinge having a spring, the spring being configured to urge return of the wiping tip to the preset orientation with respect to the rod; and
   a wiping surface attached to the wiping tip.

2. The apparatus of claim 1 wherein the handle, rod, and wiping tip comprise a unitary piece.

3. The apparatus of claim 1 wherein the wiping tip is removably attachable to the rod.

4. The apparatus of claim 1 wherein the handle is removably attachable to the rod.

5. The apparatus of claim 1 wherein the wiping surface is removably attachable to the wiping tip.

6. The apparatus of claim 1 wherein the wiping tip is tapered.

7. The apparatus of claim 1 wherein the wiping surface is a smooth cloth, cloth with large loop fibers, porous cloth, sponge like material, brush with bristles, or flexible polymer piece.

8. The apparatus of claim 1 wherein the wiping surface comprises a disposable material.

* * * * *